(12) United States Patent  
Yun et al.

(10) Patent No.: US 7,787,588 B1
(45) Date of Patent: Aug. 31, 2010

(54) SYSTEM AND METHOD FOR QUANTITATIVE RECONSTRUCTION OF ZERNIKE PHASE-CONTRAST IMAGES

(75) Inventors: Wenbing Yun, Walnut Creek, CA (US); Michael Feser, Walnut Creek, CA (US); Benjamin Hornberger, Walnut Creek, CA (US)

(73) Assignee: Xradia, Inc., Concord, CA (US)

( * ) Notice: Subject to any disclaimer, the term of this patent is extended or adjusted under 35 U.S.C. 154(b) by 0 days.

(21) Appl. No.: 12/506,946

(22) Filed: Jul. 21, 2009

Related U.S. Application Data

(60) Provisional application No. 61/082,326, filed on Jul. 21, 2008, provisional application No. 61/083,669, filed on Jul. 25, 2008.

(51) Int. Cl.
*G21K 7/00* (2006.01)
*G01N 23/00* (2006.01)
(52) U.S. Cl. .................................. 378/43; 250/311
(58) Field of Classification Search .............. 378/43, 378/50–54, 62, 63; 250/311
See application file for complete search history.

(56) References Cited

U.S. PATENT DOCUMENTS

| 6,430,254 B2 * | 8/2002 | Wilkins ............... 378/43 |
| 2003/0201393 A1 * | 10/2003 | Tsuneta et al. .......... 250/311 |
| 2008/0210868 A1 * | 9/2008 | Kohashi et al. .......... 250/311 |

OTHER PUBLICATIONS

Feser, M., et al., "Scanning Transmission X-ray Microscopy with a Segmented Detector," J. Phys. IV, France, 104 (2003), pp. 529-534.
Von Hofsten, O., et al., "Compact Zernike Phase Contrast X-Ray Microscopy Using a Single-Element Optic," Optics Letters, vol. 33, No. 9, May 2, 2008, pp. 932-934.

* cited by examiner

*Primary Examiner*—Irakli Kiknadze
(74) *Attorney, Agent, or Firm*—Houston Eliseeva, LLP

(57) ABSTRACT

The principle of reciprocity states that full-field and scanning microscopes can produce equivalent images by interchanging the roles of condenser and detector. Thus, the contrast transfer function inversion previously used for images from scanning systems can be applied to Zernike phase contrast images. In more detail, a full-field x-ray imaging system for quantitatively reconstructing the phase shift through a specimen comprises a source that generates x-ray radiation, a condenser x-ray lens for projecting the x-ray radiation onto the specimen, an objective x-ray lens for imaging the x-ray radiation transmitted through the specimen, a phase-shifting device to shift the phase of portions of x-ray radiation by a determined amount, and an x-ray detector that detects the x-ray radiation transmitted through the specimen to generate a detected image. An image processor then determines a Fourier filtering function and reconstructs the quantitative phase shift through the specimen by application of the Fourier filtering function to the detected image. As a result, artifacts due to absorption contrast can be removed from the detecting image. This corrected image can then be used in generating three dimensional (3D) images using computed tomography.

21 Claims, 5 Drawing Sheets absorption sample        phase sample
                         (phase shift $\delta \ll 360°$)

Zernike-type phase contrast
90° phase shift        270° phase shift

SYSTEM AND METHOD FOR QUANTITATIVE RECONSTRUCTION OF ZERNIKE PHASE-CONTRAST IMAGES

RELATED APPLICATIONS

This application claims the benefit under 35 USC 119(e) of U.S. Provisional Application Nos. 61/082,326, filed on Jul. 21, 2008 and 61/083,669, filed on Jul. 25, 2008, both of which are incorporated herein by reference in their entirety.

BACKGROUND OF THE INVENTION

Many imaging methods have been developed to take advantage of phase contrast. The most widely used technique with lens-based far-field microscopes is the Zernike method developed by Frits Zernike. Features that are difficult or impossible to observe in absorption contrast can be effectively studied in phase contrast mode, such as biological samples.

The set up for Zernike phase contrast imaging is similar to microscopes for absorption contrast, but a phase plate is used. The phase plate is usually placed at or near the back focal plane of the objective lens to shift the phase of the unscattered beam by $\pi/2$ or $3\pi/2$. The unscattered light then interferes with the diffracted light to produce a phase contrast image. This method has been widely used in light microscopy and x-ray microscopy, such as full-field transmission microscopes, with great success.

One drawback of Zernike phase contrast imaging is the mixing of absorption and phase contrast signals and the resulting halo-like artifacts that occur at features' edges. These artifacts can make image interpretation difficult. Thus, generally, this Zernike phase contrast imaging is usually acceptable for observing the features' morphology qualitatively, particularly in two dimensions (2D). With three dimensional (3D) imaging, e.g. computed tomography (CT) techniques, however, these artifacts will lead to severe distortions and amplified artifact structures in the 3D data. This is because the CT algorithm requires each 2D projection image to consist of the linear sum of some characteristic through the sample, e.g. the attenuation coefficient in the case of absorption contrast images. In order to effectively combine the phase-contrast imaging technique with 3D CT imaging, one must derive the linear phase shift through the sample from images that have both absorption and phase contrast signals. Another challenge is the automated separation of specimen constituents by segmentation after the tomographic reconstruction of a tilt series when these artifacts are present.

Recently, quantitative phase reconstruction from differential phase contrast images has been demonstrated in a scanning x-ray microscopy system using a segmented detector system and a Fourier filtering technique. This method inverts the contrast transfer functions of the imaging system similar to a Wiener filter.

SUMMARY OF THE INVENTION

The principle of reciprocity states that full-field and scanning microscopes can produce equivalent images by interchanging the roles of condenser and detector. Thus, the contrast transfer function inversion previously used for images from scanning systems can be applied to Zernike phase contrast images. Certain simplifications are required, like assuming the phase ring to be located in the objective plane rather than the Fourier plane, but nevertheless the method has been shown to effectively reduce artifacts in Zernike phase contrast images.

This invention pertains to a method and system for reconstructing the quantitative phase shift of the specimen from images acquired with lens-based, full-field imaging systems.

In general, according to one aspect, the invention features a full-field x-ray imaging system for quantitatively reconstructing the phase shift through a specimen. The system comprises a source that generates x-ray radiation, a condenser x-ray lens for projecting the x-ray radiation onto the specimen, an objective x-ray lens for imaging the x-ray radiation transmitted through the specimen, a phase-shifting device to shift the phase of portions of x-ray radiation by a determined amount, and an x-ray detector that detects the x-ray radiation transmitted through the specimen to generate a detected image. An image processor then determines a Fourier filtering function and reconstructs the quantitative phase shift through the specimen by application of the Fourier filtering function to the detected image. As a result, artifacts due to absorption contrast can be removed from the detecting image. This corrected image can then be used in generating three dimensional (3D) images using computed tomography, for example.

In embodiments, the x-ray radiation is between 0.2 keV and 100 keV and the source is a sealed tube, rotating anode, micro-focus, or synchrotron radiation source. Also, the condenser lens is preferably a capillary or Fresnel zone plate lens. The phase shifting device is preferably a ring-shaped transmissive device that is placed between the objective lens and the detector, such as near the back focal point of the objective lens to shift the phase by $\pi/2$ or $3\pi/2$.

In general according to other aspects, the invention is used in a full field transmission electron microscope systems and visible light microscope systems.

In general according to another aspect, the invention features a full-field x-ray imaging method. This method comprises generating x-ray radiation, projecting the x-ray radiation onto the specimen, imaging the x-ray radiation transmitted through the specimen, shifting the phase of portions of x-ray radiation by a determined amount, detecting the x-ray radiation transmitted through the specimen to generate a detected image. Then a Fourier filtering function is determined and the quantitative phase shift through the specimen is reconstructed by application of the Fourier filtering function to the detected image.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

Many types of specimens exhibit higher phase contrast than absorption contrast. For example, biological samples studied with visible light, electron, or x-ray microscopy and light metals and ceramic materials examined using x-ray microscopy can often be better analyzed using phase contrast.

Figure 1:
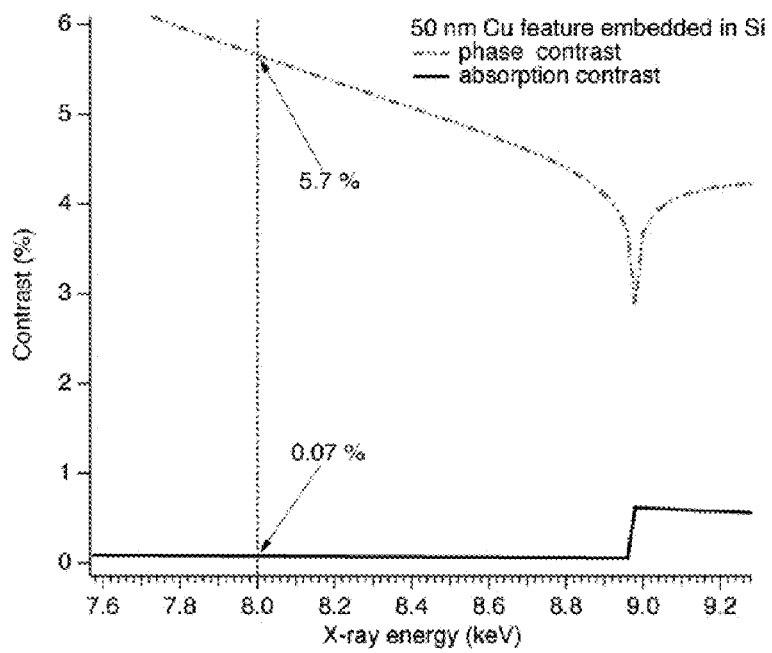
FIG. 1 is a plot of percent contrast as a function of x-ray energy (keV) of phase contrast and absorption contrast for small 50 nanometer (nm) sized features embedded in silicon.

FIG. 1 shows the phase and absorption contrast of a 50 nanometer (nm) sized copper feature in a silicon substrate for a range of different x-ray energies. The contrast is defined here as:

$$C = \frac{I_{peak} - I_{valley}}{I_{peak} + I_{valley}}.$$

Note that absorption generates relatively weak contrast except at copper's absorption edge at 9 keV. In comparison, phase contrast dominates with sometimes several orders of magnitude higher contrast. This advantage in intrinsic contrast makes phase contrast better suited for imaging specimens by bringing benefits of lower dose, shorter exposure time, and better image quality.

Figure 2:
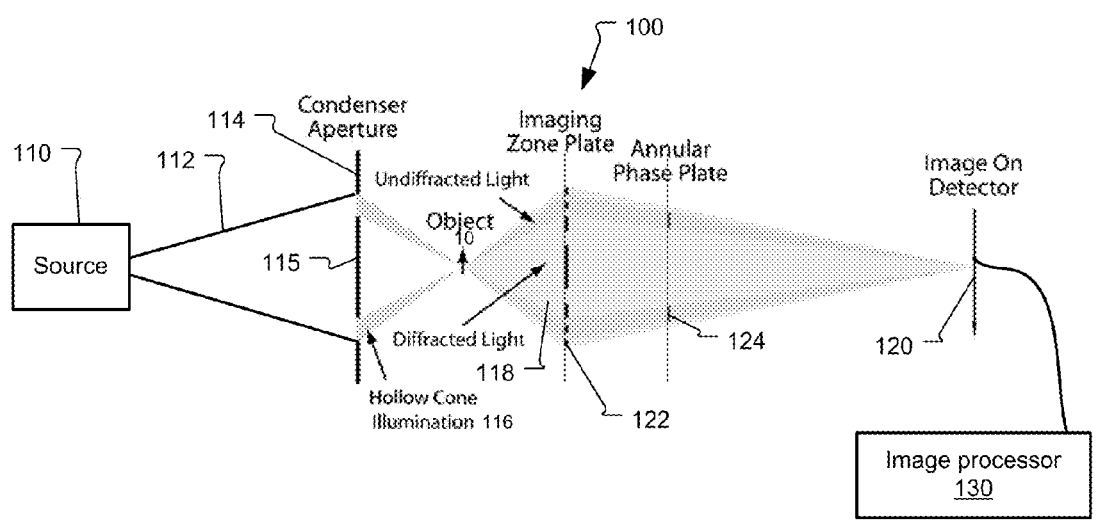
FIG. 2 is a schematic illustration of a full-field imaging microscope with a phase ring for Zernike phase contrast imaging.

FIG. 2 shows a typical full-field imaging microscope 100.

Radiation 112 is generated by a radiation source 110. Typically, this radiation is intrinsically narrowband radiation or broadband radiation that is filtered by a bandpass filter to be narrowband.

In the example of a transmission x-ray microscope, the radiation is x-ray radiation having an energy between 0.2 keV and 100 keV. Further, the source 110 is preferably a sealed tube source, a rotating anode x-ray source, a micro-focus x-ray source, or a synchrotron radiation source.

In the example of an electron microscope, the source 110 generates radiation that is an electron beam, having an energy between 100 keV and 1 MeV.

In the example of an optical microscope, the source 110 generates radiation in the optical frequencies including infrared, visible light, or ultraviolet.

A condenser lens 114 collects the radiation 112 from the source 110. The condenser lens 114 projects the illumination beam onto the specimen or object 10. The aperture of the condenser lens 114 forms a hollow cone of converging radiation 116.

In example of an x-ray microscope, the condenser lens 114 is a capillary tube or lens with ellipsoidal shape or paraboloidal shape. In other examples, the condenser lens is a Fresnel zone plate lens. In either example, a center beam stop 115 is employed to create the aperture required to produce the hollow cone illumination pattern 116.

In the example of an electron microscope, the condenser lens 114 is beam shaping magnets and a central beam stop.

In the example of an optical microscope, common refractive lenses or curved mirrors are used as the condenser lens 114.

The beam (118) passing through the specimen 10 is imaged to a spatially resolved detector 120 by the objective lens 122, which is typically a Fresnel zone plate lens. The transmitted radiation 118 includes light that was undiffracted by the object 10 and light that was diffracted by the object 10.

In the example of an optical microscope, common refractive lenses or curved mirrors are again used as the objective lens 122.

Typically, the spatially resolved detector 120 has a high resolution having greater than 1024×1024 pixels. In some cases, a direct detection scheme is used in which a CCD detector or other electronic detector is used to detect the radiation, when optical frequencies or soft x-rays are used. However, with higher energies intervening scintillators are employed to enable detection of the radiation by first converting into the optical frequencies.

An annular or ring-shaped phase plate 124, between the objective lens 122 and the detector 120, phase shifts the light that is undiffracted by the sample relative to the light that is diffracted by the sample so that they interfere with each other at the detector 120.

Typically, the phase plate 124 is placed near the back focal point of the objective lens 122. The material of the phase plate and its thickness relative to the wavelength of the source radiation 112 has the effect of shifting the phase of the radiation transmitted through the phase plate 124 by typically $\pi/2$ or $3\pi/2$.

FIGS. 3A-3D show the advantages of the Zernike phase contrast imaging mode.

Figure 3A:
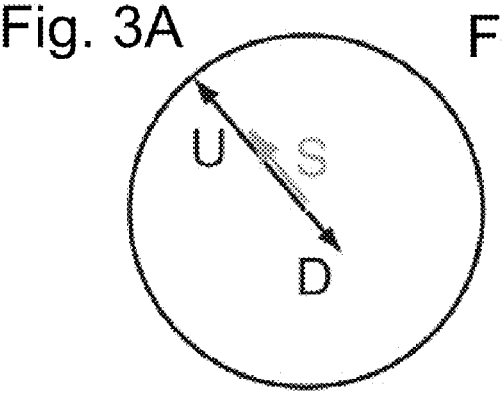
FIGS. 3A-3D are phasor diagrams of Zernike phase contrast imaging modes.
Figure 3B:
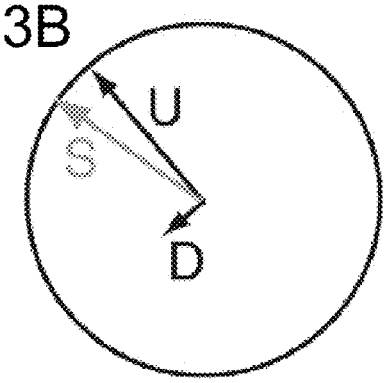

FIG. 3A is the phasor diagram for an absorption sample; the diffracted (D) wave has the same phase as the undiffracted (U) wave, so that the sum (S) wave has a smaller amplitude than the undiffracted wave, resulting in absorption contrast. However, as shown in FIG. 3B, when a phase sample is imaged using standard absorption contrast, the D wave is 90 degrees phase shifted relative to the U wave, so that the S wave has approximately the same amplitude as the U wave, resulting in very weak absorption contrast.

Figure 3C:
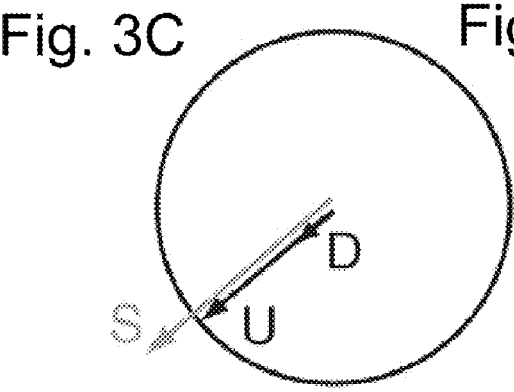
Figure 3D:
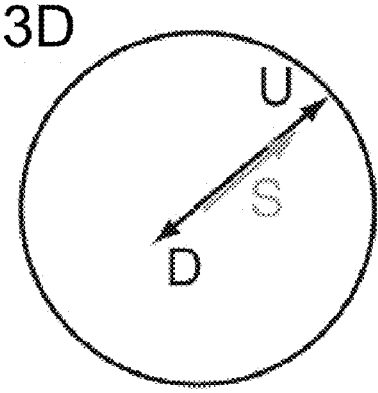

In the Zernike type microscope, the U wave is phase shifted by 90 degrees (positive Zernike contrast), so that the S wave has an amplitude different from the U wave as shown in FIG. 3C. The phase shift of the specimen has been transformed into an intensity difference in the image, resulting in Zernike phase contrast. FIG. 3D shows negative Zernike contrast in which the phase shift is 270 degrees.

The phase-contrast imaging method employed by the image processor 130 applies the Principle of Reciprocity to apply Fourier filtering to obtain quantitative phase-contrast images with full-field microscopes operating in Zernike phase contrast mode so as to compensate for the presence of the absorption contrast signals with the phase contrast signals.

In more detail, an image processor 130 receives the combined phase and absorption contrast image generated by the detector 120 and processes the image by calculating the Fourier filtering function and reconstructing the quantitative phase shift through the specimen 10 by application of Fourier filtering function to the image recorded by the detector 120.

In more detail, based on this geometry, the Fourier filtering is carried out in the following process:

$S_k(f)=H_r(f)T_r^k(f)+iH_i(f)T_i^k(f)+N_k(f).$

This equation describes the imaging process (assuming a weak specimen approximation), where $S_k(f)$ is the image recorded by detector segment k in the Fourier space; $H_r(f)$ and $H_i(f)$ are the Fourier transforms of the real and imaginary parts of the specimen transmission function (related to specimen absorption and phase shift); $T_r^k(f)$ and $T_i^k(f)$ are the transfer functions for the specimen real and imaginary parts; and $N_k(f)$ is the spectral noise. The Fourier filter is calculated by the image processor 130 by minimizing the reconstruction error:

$$W_k(f) = \frac{T_r^{(k)*}(f)}{\sum_l |T_r^l(f)|^2 + \beta_r^l(f)} + \frac{T_i^{(k)*}(f)}{\sum_l |T_i^l(f)|^2 + \beta_i^l(f)},$$

where $\beta_i^l(f)$ are the noise parameters, describing the strength of the specimen spectrum relative to the noise level. The best estimate of the specimen can then be calculated as $$H(f) = \sum_k W_k(f) \times S_k(f).$$

Using the Principle of Reciprocity, image processor 130 calculates the filter function for a typical transmission microscope by replacing the segmented detector from the scanning microscope with the illumination (condenser) in the full-field case, and adding the phase ring to the pupil for the full-field case.

Again from the principle of reciprocity it follows that the Zernike method can be transferred to a scanning microscope by adding a phase ring to the pupil and using an annular detector matching the phase ring. Again, the Fourier filtering technique can be applied in this case to reconstruct the quantitative specimen phase shift from the resulting image.

FIGS. 4A-4F show simulated illumination and phase ring patterns typically used in a Zernike phase contrast imaging system and resulting contrast transfer function (CTF) and reconstruction filter functions.

Figure 4A:
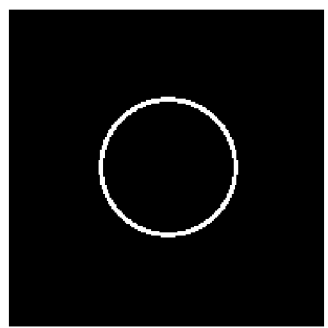
FIGS. 4A-4F show simulated illumination and phase ring patterns typically used in a Zernike phase contrast imaging system and resulting contrast transfer function (CTF) and reconstruction filter functions.

FIG. 4A shows the illumination pattern from source.

Figure 4B:
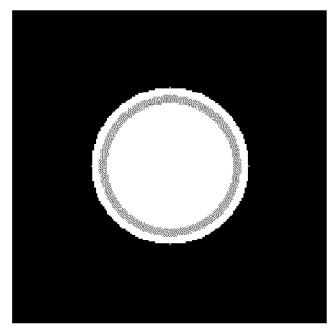

FIG. 4B shows the illumination pupil with phase ring pattern.

Figure 4C:
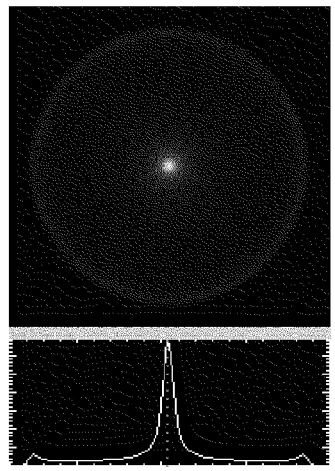

FIG. 4C shows the real part of the CTF.

Figure 4D:
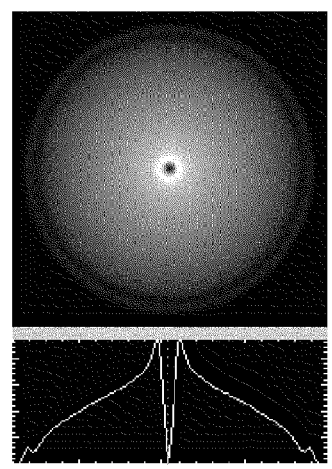

FIG. 4D shows the imaginary part of the CTF

Figure 4E:
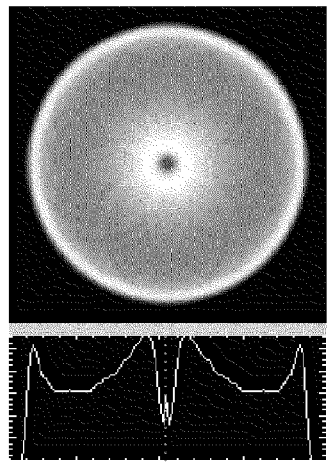

FIG. 4E shows the real part of the reconstruction filter.

Figure 4F:
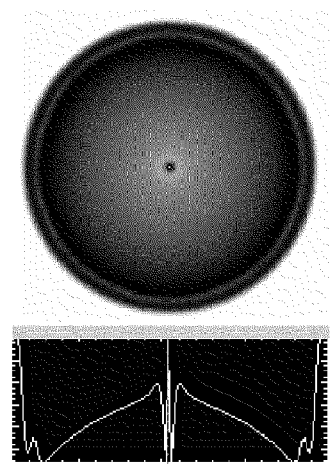

FIG. 4F shows the imaginary part of the reconstruction filter.

Figure 5A:
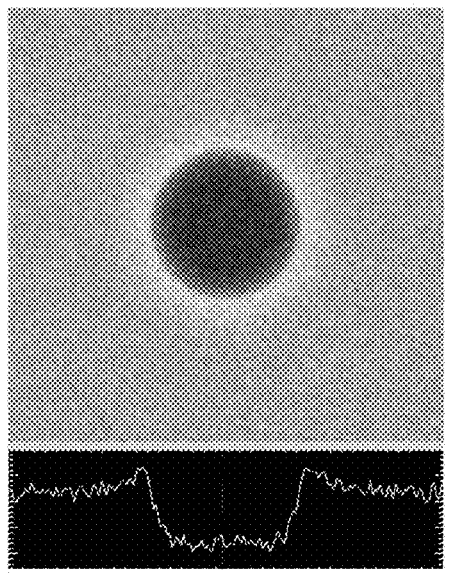
FIGS. 5A and 5B show a simulated Zernike image of a gold sphere and the corresponding phase reconstruction after applying the reconstruction filter, respectively.
Figure 5B:
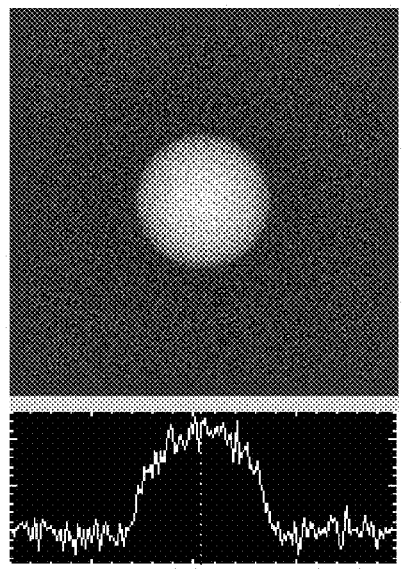

FIG. 5A shows a simulated image of a gold sphere that would be obtained from a typical transmission x-ray microscope using Zernike phase contrast. Applying the filter function shown in FIGS. 4E and 4F, a phase image of the sphere is produced as shown in FIG. 5B.

Figure 6A:
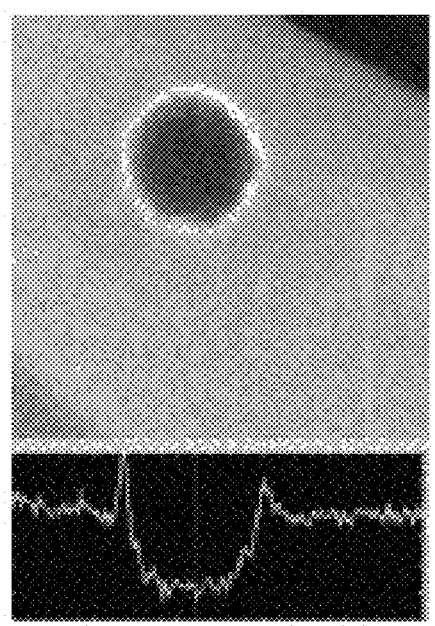
FIGS. 6A and 6B show images of a gold sphere acquired with a transmission x-ray microscope and the quantitative phase images reconstructed with the Fourier filtering technique, respectively.
Figure 6B:
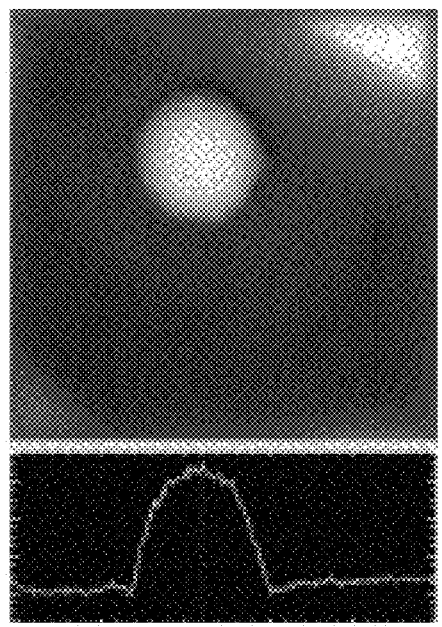

FIG. 6A shows an actual image acquired with the actual transmission x-ray microscope (TXM) with 50 nm resolution. By applying the same filter function, the quantitative phase image is produced as shown in FIG. 6B.

Figure 7:
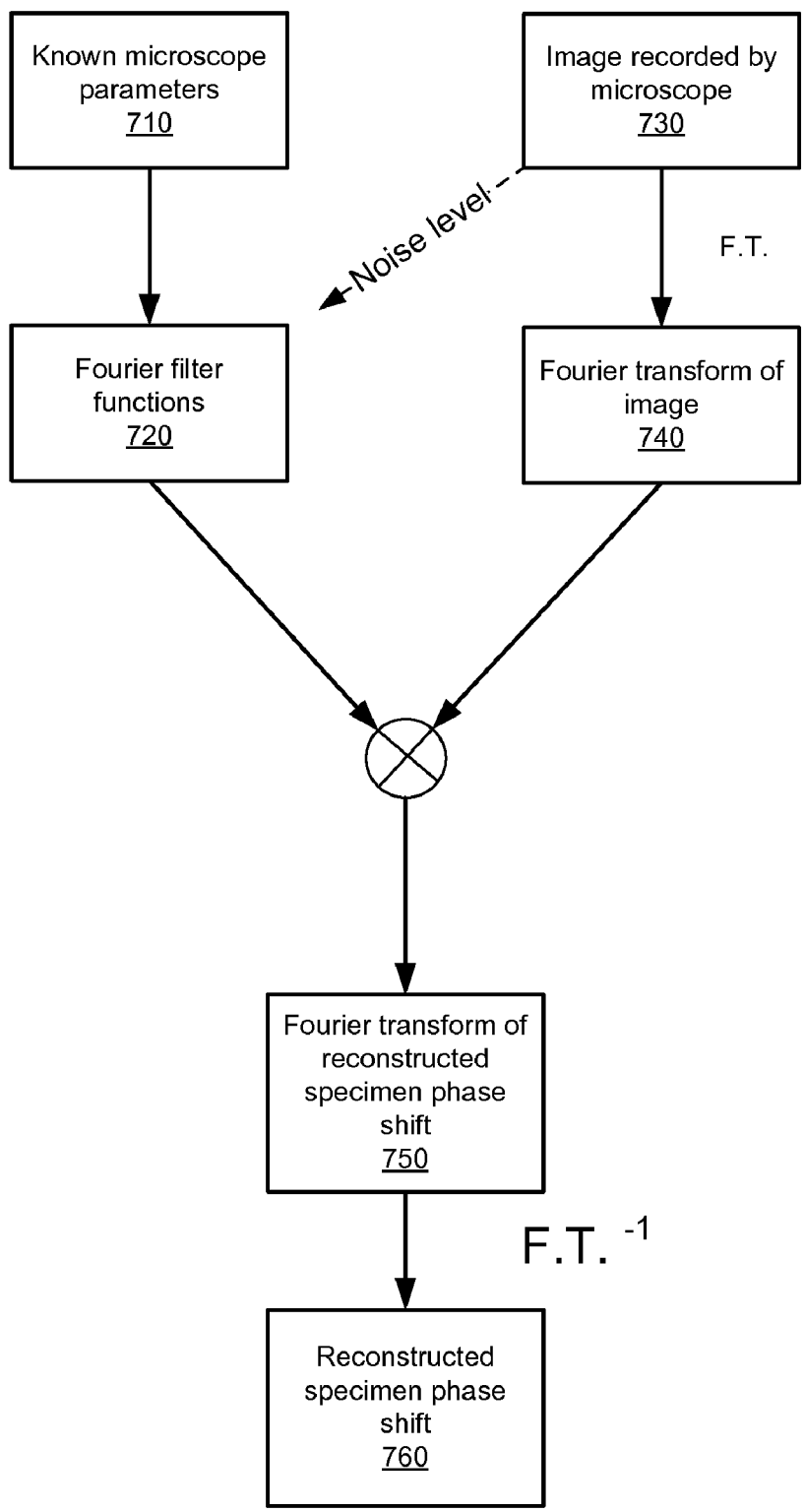
FIG. 7 is a flow diagram showing the filtering process performed by the image processor 130 to generate the reconstructed specimen phase shift.

FIG. 7 summarizes the filtering process performed by the image processor 130.

In step 710, known microscope parameters are collected. These include characteristics of the illumination pattern, objective, and the phase ring. From this information, the Fourier filter functions are derived in step 720. Also impacting the filter functions is an estimate of the noise level in the image recorded by the microscope 100.

In step 730, the image is recorded by the microscope 100, which includes both phase and absorption contrast signals. Then, in step 740, a Fourier transform of the image is generated.

The Fourier filter functions, which were derived in step 720, are applied to the Fourier transform of the image to generate the Fourier transform of the reconstructed specimen phase shift in step 750. Finally, application of the inverse Fourier transform yields the reconstructed specimen phase shift in step 760.

While this invention has been particularly shown and described with references to preferred embodiments thereof, it will be understood by those skilled in the art that various changes in form and details may be made therein without departing from the scope of the invention encompassed by the appended claims.

What is claimed is:

1. A full-field x-ray imaging system for quantitatively reconstructing the phase shift through a specimen, the system comprising:
   a source that generates x-ray radiation;
   a condenser x-ray lens for projecting the x-ray radiation onto the specimen;
   an objective x-ray lens for imaging the x-ray radiation transmitted through the specimen;
   a phase-shifting device to shift the phase of portions of x-ray radiation by a determined amount;
   an x-ray detector that detects the x-ray radiation transmitted through the specimen to generate a detected image; and
   an image processor that determines a Fourier filtering function and reconstructs the quantitative phase shift through the specimen by application of the Fourier filtering function to the detected image.

2. An x-ray imaging system as claimed in claim 1, where the x-ray radiation is between 0.2 keV and 100 keV.

3. An x-ray imaging system as claimed in claim 1, wherein the source is a sealed tube source.

4. An x-ray imaging system as claimed in claim 1, wherein the source is a rotating anode x-ray source.

5. An x-ray imaging system as claimed in claim 1, wherein the source is a micro-focus x-ray source.

6. An x-ray imaging system as claimed in claim 1, wherein the source is a synchrotron radiation source.

7. An x-ray imaging system as claimed in claim 1, wherein the condenser lens is a capillary lens with ellipsoidal shape.

8. An x-ray imaging system as claimed in claim 1, wherein the condenser lens is a capillary lens with paraboloidal shape.

9. An x-ray imaging system as claimed in claim 1, wherein the condenser lens is a Fresnel zone plate lens.

10. An x-ray imaging system as claimed in claim 1, wherein the objective lens is a Fresnel zone plate lens.

11. An x-ray imaging system as claimed in claim 1, wherein the phase shifting device is a ring-shaped transmissive device.

12. An x-ray imaging system as claimed in claim 1, wherein the phase ring is placed between the objective lens and the detector.

13. An x-ray imaging system as claimed in claim 1, wherein the phase ring is placed near the back focal point of the objective lens.

14. An x-ray imaging system as claimed in claim 1, wherein the phase ring shifts the phase by $\pi/2$ or $3\pi/2$.

15. A transmission electron microscope system for quantitatively reconstructing the phase shift through a specimen, the system comprising:
- a source that generates an electron beam;
- a condenser lens for projecting the electron beam onto the specimen;
- an objective lens for imaging the electron beam transmitted through the specimen;
- a phase-shifting device to shift the phase of portions of electron beam by a determined amount;
- a detector that detects the x-ray radiation transmitted through the specimen to generate a detected image; and
- an image processor that determines a Fourier filtering function and reconstructs the quantitative phase shift through the specimen by application of the Fourier filtering function to the detected image.

16. An electron microscope system as claimed in claim 15, wherein the electron beam has an energy between 100 keV and 1 MeV.

17. An electron microscope system as claimed in claim 15, wherein the phase shifting device shifts the phase by $\pi/2$ or $3\pi/2$.

18. An electron microscope system as claimed in claim 15, wherein the phase shifting device is placed between the objective lens and detector.

19. An electron microscope system as claimed in claim 15, wherein the phase ring is placed near the back focal point of the objective lens.

20. A full-field x-ray imaging method for quantitatively reconstructing the phase shift through a specimen, the method comprising:
- generating x-ray radiation;
- projecting the x-ray radiation onto the specimen;
- imaging the x-ray radiation transmitted through the specimen;
- shifting the phase of portions of x-ray radiation by a determined amount;
- detecting the x-ray radiation transmitted through the specimen to generate a detected image; and
- determining a Fourier filtering function; and
- reconstructing the quantitative phase shift through the specimen by application of the Fourier filtering function to the detected image.

21. An x-ray imaging method as claimed in claim 20, where the x-ray radiation is between 0.2 keV and 100 keV.

* * * * *